United States Patent [19]
Dame

[11] Patent Number: 5,193,977
[45] Date of Patent: Mar. 16, 1993

[54] FLEXIBLE MEMBRANE SEALLESS CENTRIFUGAL PUMP

[76] Inventor: Don Dame, 6740 Ashwood Rd. #203, Woodbury, Minn. 55125

[21] Appl. No.: 797,118

[22] Filed: Nov. 22, 1991

[51] Int. Cl.⁵ .............................................. F04D 29/66
[52] U.S. Cl. ..................................... 415/206; 417/413;
417/423.11; 415/900; 415/141; 600/16; 623/3;
277/212 FB; 277/212 C
[58] Field of Search .......................... 417/413, 423.11;
415/206, 203, 900, 140, 141, 170.1; 600/16, 18;
623/3; 277/212 R, 212 C, 212 F, 212 FB, 133, 134

[56] References Cited

U.S. PATENT DOCUMENTS

| | | |
|---|---|---|
| 1,441,794 | 1/1923 | Germain . |
| 1,501,870 | 7/1924 | Schranz . |
| 1,514,968 | 11/1924 | Hull . |
| 2,119,955 | 6/1938 | Litton . |
| 2,419,074 | 4/1947 | Herbert, Jr. . |
| 2,497,867 | 2/1950 | Cymmer . |
| 2,551,847 | 5/1951 | Nelson . |
| 2,610,525 | 9/1952 | Sprigg . |
| 2,773,453 | 12/1956 | Gemeinhardt . |
| 2,860,933 | 11/1958 | Wolff . |
| 2,931,189 | 4/1960 | Sigworth . |
| 2,943,495 | 7/1960 | Musser . |
| 3,097,366 | 7/1963 | Winchell ............................. 623/3 |
| 3,132,525 | 5/1964 | Davids . |
| 3,157,054 | 11/1964 | Dean . |
| 3,232,126 | 2/1966 | Pucciarello et al. . |
| 3,311,354 | 3/1967 | Wilson . |
| 3,457,795 | 7/1969 | Hamren . |
| 3,879,151 | 4/1975 | Majewicz . |
| 3,947,156 | 3/1976 | Becker ............................. 417/413 |
| 4,384,829 | 5/1983 | Conley et al. ........................ 623/3 |
| 4,403,521 | 9/1983 | f'Geppert . |
| 4,722,660 | 2/1988 | Akamatsu . |
| 5,006,104 | 4/1991 | Smith et al. ............................. 623/3 |

OTHER PUBLICATIONS

*Artificial Organs,* 13(5):486–492, Raven Press, Ltd., New York "Communications/Abstracts . . . Int'l Workshop on Rotary Pumps".

Primary Examiner—Edward K. Look
Assistant Examiner—Mark Sgantzos
Attorney, Agent, or Firm—Peterson, Wicks, Nemer & Kamrath

[57] ABSTRACT

Centrifugal pumps (10) are disclosed having nonrotatable membranes (21) to rotate fluid in a pumping chamber having at least a first open passage inlet (71) and an open passage outlet (91). Specifically, the membrane (21) is deflected into a nonconcentric shape to the fluid rotation, with the nonconcentric shape being rotated to function as a centrifugal pump impeller by deformers (41, 42, 43) separated from the pumped fluid by the membrane (21). As the membrane (21) does not rotate, rotary shaft seals, bearings, or small gaps between moving, sliding, and/or rubbing pump surfaces and to which the pumped fluid is accessible are not required in the pumps (10). In preferred forms, the deformers (41, 42) can be located inside the membrane (21) and inside the pumping chamber or the deformer (43) can be located outside the membrane (21) and outside the pumping chamber. The membranes (21) are corrugated (102, 103) in the preferred form to direct the fluid flow into a rotary motion and to provide directional stiffness/flexibility characteristics. Secondary membranes (31) can be provided to cover the membrane (21) to prevent leaking and/or for ease of cleaning or sterilization. When the membrane (21) extends inside of the pumping chamber, a tube liner (51) can be provided inside of the membrane (21) and the deformer (41) to act as the primary inlet (81) or as a secondary inlet (81) with the housing inlet (71).

51 Claims, 3 Drawing Sheets

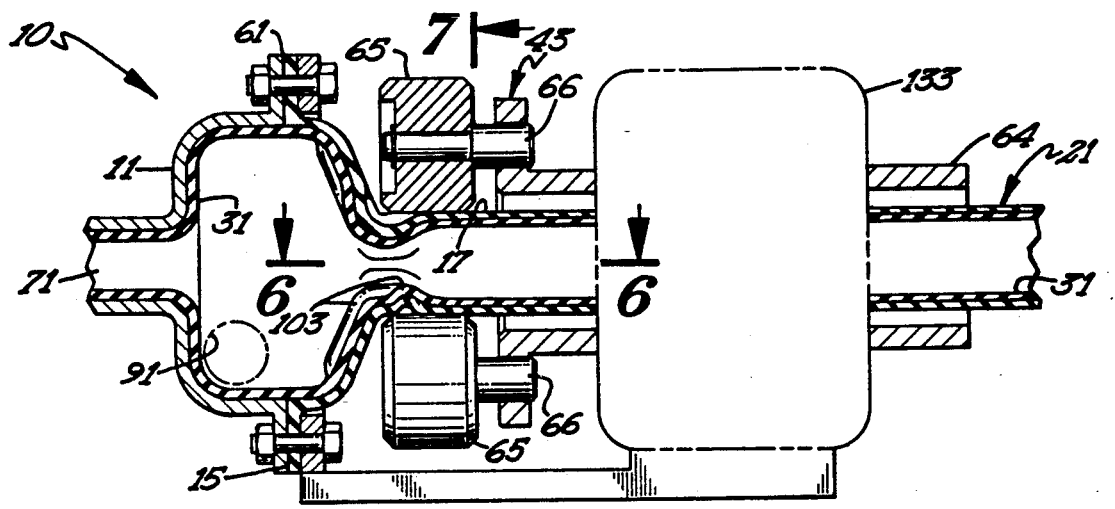
Fig 5
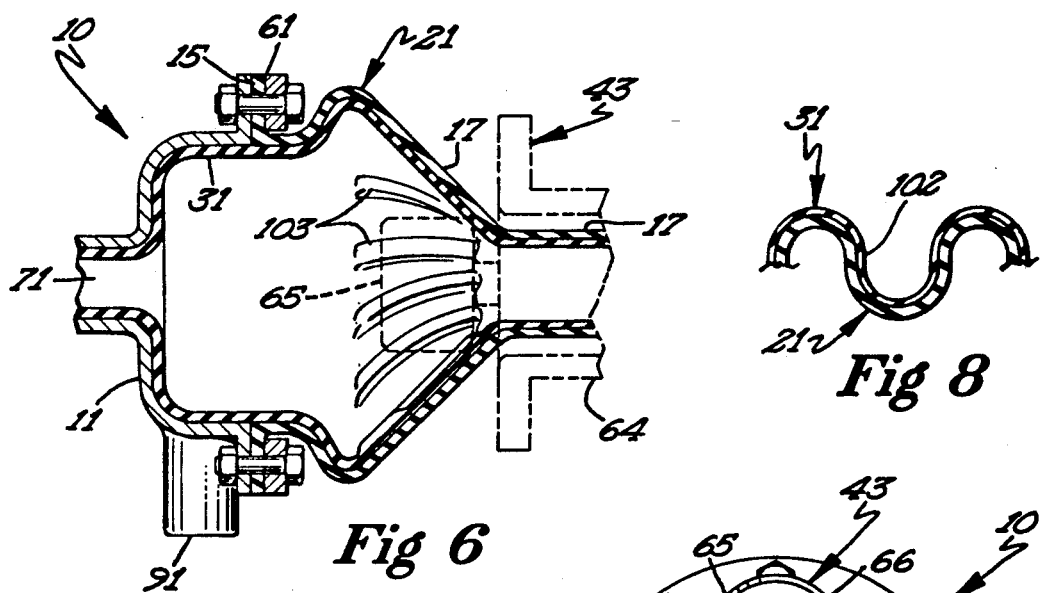
Fig 6
Fig 8
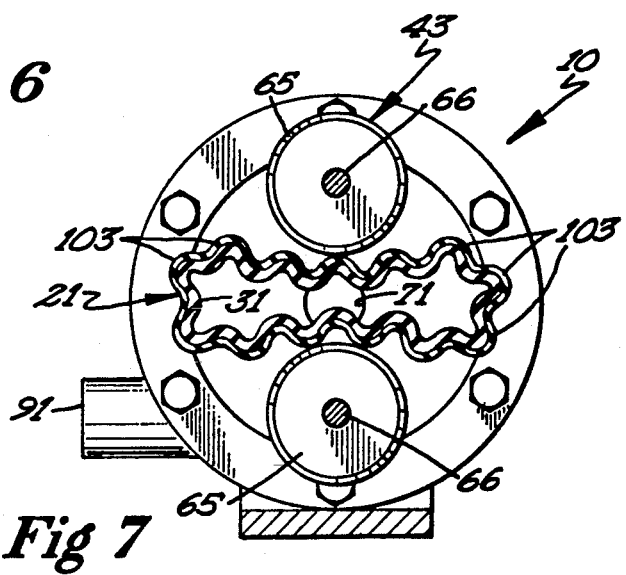
Fig 7

FLEXIBLE MEMBRANE SEALLESS CENTRIFUGAL PUMP

BACKGROUND

The present invention relates generally to pumps, particularly to pumps which do not force the fluid being pumped into a small gap between moving, sliding and/or rubbing structural pump surfaces inside the pump, and specifically to centrifugal pumps not requiring or using conventional rotating shaft seals or bearings in the pumped fluid.

Virtually all pumps, since the beginning of time, have had a "fundamental flaw", which causes most of the major pump problems. The "fundamental flaw" is that the fluid being pumped has always been forced into the small gap between some moving, sliding, and/or rubbing structural pump surfaces inside the pump, whether the pump is of the centrifugal or positive displacement type. This often causes serious problems for the pump operator.

Specifically, the primary cause of centrifugal pump failures is the failure of the rotating drive shaft seal. The shaft seal is necessary to seal the area where the rotating drive shaft enters the pressurized pump case. All rotating shaft seals operate in the same way, with the same fundamental flaw. All rotating shaft seals try to slide a moving seal surface very tightly against a stationary seal surface, so that fluid can not leak through the small gap between the moving and stationary surfaces. But there is always at least a microscopic gap between the seal surfaces where fluid can leak through. Sometimes the leaks become very large.

The U.S. Environmental Protection Agency has determined that the average chemical pump leaks 1000 pounds (375 kilograms) per year through "average" rotating shaft seals. Industrial quality pumps have their mechanical shaft seals fail every 89 days on average. Even the best medical quality centrifugal blood pumps have their shaft seals fail within 30 days.

Magnetic drive pumps were developed to eliminate the leaky, sliding surfaces of the rotating shaft seal. The sliding surfaces in the pumped fluid were not eliminated but were simply moved to a new location as the internal rotor support bearings. Problems with the internal sliding bearing surfaces include an inability to run dry for any length of time, any abrasives in the pumped fluid will wear out the bearings, and attempting to pump a fragile fluid such as blood will cause unacceptable damage because the blood cells will be destroyed by the grinding action of the sliding bearing surfaces. The magnetic drive pump is now the only "sealless" centrifugal pump design which is commercially available, but its high cost and unsatisfactory operating characteristics have limited its usefulness.

Magnetic bearings are sometimes used in place of sliding bearings to support the rotor in pumps including magnetic drive pumps. Magnetic bearing pumps will continue to have the fundamental flaw of all conventional pumps. The magnetic bearings will require a "close moving clearance" within the pumped fluid. Magnetic bearing pumps are inherently complicated, expensive, heavier, and inefficient, with a lower bearing load capacity than other conventional pumps.

Positive displacement pumps operate by mechanically forcing the pumped fluid from the low pressure zone to a high pressure zone and require some kind of sliding and/or moving surface to function as a valve to prevent fluid backflow. The valve can clog or can be damaged by abrasives in the fluid, or the valve can damage fragile fluids such as blood.

It can then be appreciated that previous attempts to correct the fundamental flaw only succeeded in relocating the sliding pump surface to a different place within the pumped fluid, which never really corrected the problem. Pump operators have always wanted to completely eliminate this fundamental flaw that causes so many pump problems, but no one else has ever been able to do so.

Thus, a need exists in the field of fluid pumping for completely eliminating the moving, sliding, and/or rubbing pump surfaces within the pumping chamber to provide many operating benefits. Further, a need exists for pumps which can be manufactured at a lower cost than conventional pumps.

SUMMARY

These and other needs and problems in the field of fluid pumping have been overcome by the present invention by providing, in the preferred form, a pump where fluid entering a pumping chamber through an open passage fluid inlet is rotated in the pumping chamber with a tangential velocity to generate a centrifugal force and be discharged from the pumping chamber through an open passage fluid outlet by a membrane which defines at least a portion of the pumping chamber and which is deformed by means outside the pumping chamber.

In a preferred aspect, the membrane for the pump includes means for substantially preventing deflection of the membrane in at least first directions while allowing flexing in other directions in order to deform the membrane into a nonconcentric shape relative to the center of fluid rotation.

In further aspects of the present invention, the membrane includes means for directing fluid flow to transfer rotary motion of a deformed, nonconcentric shape in the membrane to the fluid in the pumping chamber.

In a preferred form, the deforming means is located inside of the membrane, and a tube liner is located in the interior of the tube allowing fluid flow to the pumping chamber through the membrane.

It is thus an object of the present invention to provide a novel pump.

It is further an object of the present invention to provide such a novel pump not requiring a rotating shaft seal which is the largest cause of pump failure.

It is further an object of the present invention to provide such a novel pump which will prevent leaks out of the pump which can cause environmental damage or economic damage due to the loss of pumped material.

It is further an object of the present invention to provide such a novel pump which will prevent leaks into the pump which may adversely affect the fluid being pumped such as contaminated air or bacteria leaking into a chemical, food, drug, or medical pump.

It is further an object of the present invention to provide such a novel pump which handles the fluid in a very gentle manner suitable for handling food, drugs, chemicals, and like materials without damage.

It is further an object of the present invention to provide such a novel pump which eliminates the requirement for injecting a sealing fluid into the rotating shaft seal area to flush away troublesome material.

It is further an object of the present invention to provide such a novel pump which eliminates the requirement of bearings and close fits in the pumped fluid such as bearings required to support the rotating impeller in magnetic drive sealless pumps or inlet and/or discharge valves and other close moving clearances in positive displacement pumps.

It is further an object of the present invention to provide such a novel pump suitable for pumping abrasives without damage.

It is further an object of the present invention to provide such a novel pump suitable for pumping trash or other clogging and/or stringy material.

It is further an object of the present invention to provide such a novel pump suitable for sterile applications requiring ease of cleaning.

It is further an object of the present invention to provide such a novel pump capable of pumping a high percentage of vapor bubbles without becoming "vaporlocked".

It is further an object of the present invention to provide such a novel pump which is not prone to cavitation problems.

These and further objects and advantages of the present invention will become clearer in light of the following detailed description of illustrative embodiments of this invention described in connection with the drawings.

DESCRIPTION OF THE DRAWINGS

The illustrative embodiments may best be described by reference to the accompanying drawings where:

FIG. 5 shows a cross sectional view of an alternate embodiment of a flexible membrane sealless centrifugal pump according to the preferred teachings of the present invention.

FIG. 6 shows a cross sectional top view of the flexible membrane sealless pump of FIG. 5.

FIG. 7 shows a cross sectional view of the flexible membrane sealless pump of FIG. 5 according to section line 7—7 of FIG. 5.

FIG. 8 shows a fragmentary cross sectional view of the flexible membrane sealless pump of FIG. 3 according to section line 8—8 of FIG. 4.

Figure 1:
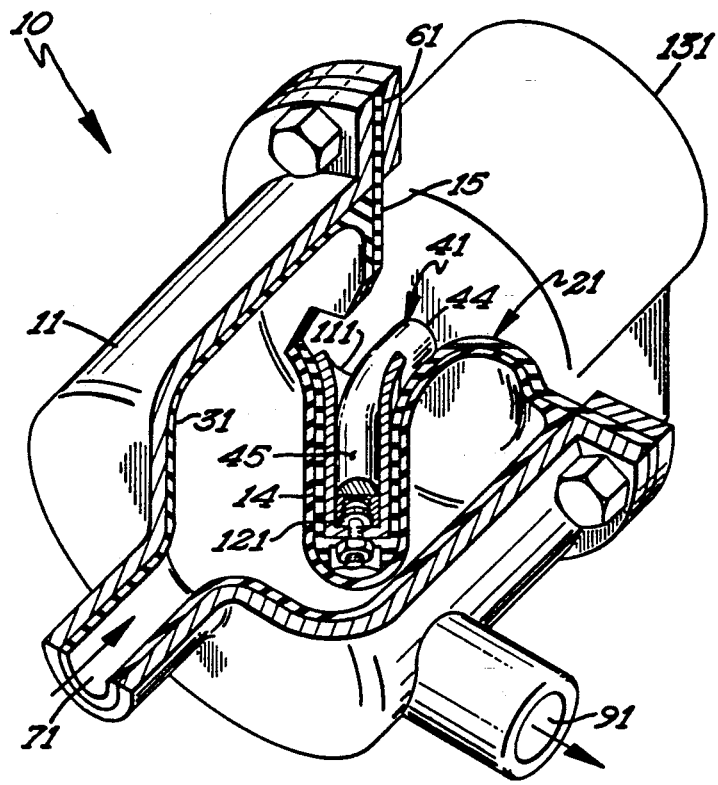
FIG. 1 shows a perspective view of a flexible membrane sealless centrifugal pump according to the preferred teachings of the present invention, with portions being broken away to show constructional details.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "end", "inner", "first", "second", "inside", "outside", and similar terms are used herein, it should be understood that these terms have reference only to the structure shown in the drawings as it would appear to a person viewing the drawings and are utilized only to facilitate describing the invention.

DESCRIPTION

Flexible membrane sealless centrifugal pumps according to the preferred teachings of the present invention are shown in the drawings and generally designated 10. Pumps 10 generally include a pump housing 11 which defines a pumping chamber to contain the fluid to be pumped. In the preferred form, one end of pump housing 11 is closed off with a nonrotatable, flexible, fluid-impervious, primary membrane 21. One or more flexible, fluid-impervious, secondary membranes 31 can be provided inside the pumping chamber and extending over housing 11 and/or primary membrane 21 or portions thereof. In the preferred form, membrane 21 includes a tube 14 having an end integrally connected to an annular flange 15. Flange 15 of membrane 21 is sealed to pump housing 11 with a static seal 61.

Pumps 10 further include a fluid inlet 71 in the form of a continuously open passage for the fluid and which in the preferred form is generally located in the end of pump housing 11 near the center of fluid rotation. Pumps 10 further include a fluid outlet 91 located away from the center of fluid rotation and in the form of a continuously open passage for the fluid, with outlet 91 in the preferred form extending tangentially from the cylindrical side of pump housing 11.

Figure 2:
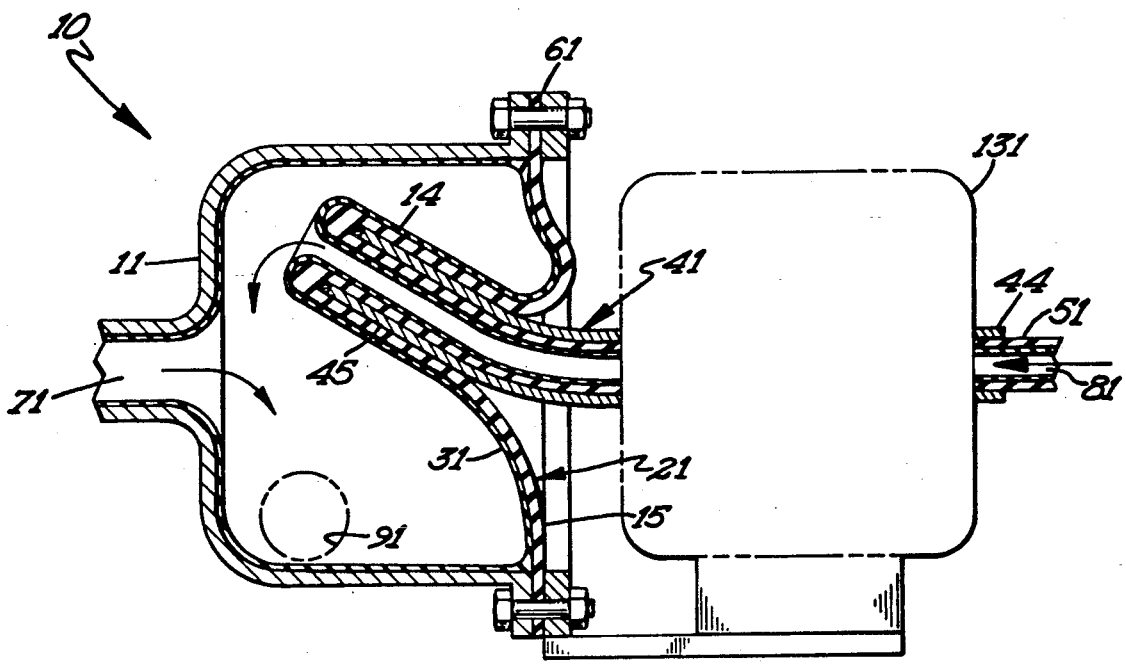
FIG. 2 shows a cross sectional view of an alternate embodiment of a flexible membrane sealless centrifugal pump according to the preferred teachings of the present invention.

A first preferred form of pump 10 is shown in FIGS. 1 and 2 with tube 14 in generally the form of a hose 14 having an open end, an interior, and general circular cross sections of equal size. Hose 14 extends into the pumping chamber. Pump 10 further includes a deformer 41 located outside of the pumping chamber and inside the interior of hose 14 for deforming membranes 21 and 31 to rotate the fluid in the pumping chamber about a center of fluid rotation. In the preferred form, deformer 41 includes a driving shaft 44 integrally connected to a shaft extension 45 extending at a nonparallel angle therefrom and particularly in the most preferred form at an obtuse angle in the order of 120°. Shaft extension 45 has a size and shape generally complementary to and for slideable receipt in hose 14. Shaft 44 extends through the open end of hose 14 and is rotated about an axis extending along the center of fluid rotation by any suitable means such as an electric motor 131, with motor 131 also providing the bearings to support and center shaft 44 in pump housing 11 in the most preferred form. It can then be appreciated that with shaft 44 positioned along the center of fluid rotation, shaft extension 45 deflects hose 14 into a nonsymmetrical, nonconcentric shape from the center of fluid rotation.

Now that the basic construction of deformer 41 according to the preferred teachings of the present invention has been set forth, the operation and subtle features of pump 10 can be explained and appreciated. Specifically, the fluid to be pumped enters pump housing 11 through fluid inlet 71 in a low pressure zone of the pumping chamber. The rotation of driving shaft 44 by motor 131 rotates the nonconcentric, nonsymmetrical shape of hose 14 as deflected by deflector 41. The nonconcentric shape has a size and configuration to efficiently transfer energy to the fluid and maximize the tangential velocity of the rotating fluid (while minimizing radial and axial fluid velocities) with the rotation of the nonconcentric, nonsymmetrical shape functioning as a rotating pump impeller causing the fluid inside the pumping chamber to rotate. The fluid rotating within the enclosed pumping chamber generates a pumping force or pressure, due to the well known principle of centrifugal force, which is generated within all rotating fluids. Using the same fluid mechanics physical laws which are used in all other centrifugal pumps, the fluid is discharged from pump housing 11 through fluid outlet 91 located in a higher pressure zone of the pumping chamber in the same manner as a conventional centrifugal pump design. Fluid outlet 91 should generally be located as far away from the center of fluid rotation as possible to maximize fluid discharge pressure and pump efficiency.

It should then be noted that although the nonconcentric, nonsymmetrical shape, shaft 44, and shaft extension 45 rotate, membranes 21 and 31 do not rotate but rather are deflected or flexed. Thus, static seal 61 can be utilized for membranes 21 and 31, with static seals 61 being relatively trouble free. Particularly, troublesome rotating shaft seals are not required to separate the fluid from the environment and/or movable parts of pump 10.

It can further be appreciated that although membranes 21 and 31 do not rotate, relative movement does occur between membrane 21 and shaft extension 45 of deformer 41. Suitable provisions such as bearings 111 and 121 can be provided to reduce wear and friction between membrane 21 and deformer 41. Particularly, bearing 111 reduces friction and wear to membrane 21 due to radial loads and is shown in the preferred form as a sock of a size for slideable receipt inside of tube 14 and for slideable receipt on shaft extension 45, and having an enlarged open end to compensate for the increased flexing at the interconnection of extension 45 to shaft 44. Bearing 111 is formed of suitable bearing material which may be a rigid bearing surface or may be a flexible, wear-resistant material such as a woven, flexible, wear-resistant mesh. Relative movement would then occur between bearing 111 and deformer 41 and would be minimized between bearing 111 and membrane 21. It should be understood that bearing 111 could take other forms providing rolling, sliding or other bearing support such as a flexible helical coil. Likewise, bearing 111 could be included on the inner surface of membrane 21 and/or on the outer surface of shaft extension 45 of deformer 41, such as metal segments embedded in the inner surface of membrane 21 to provide a wear resistant bearing surface. Similarly, bearing 121 reduces friction and wear to membrane 21 due to axial or thrust loads and is shown in the preferred form as sandwiched between the free end of shaft extension 45 and membrane 21. Further, in the preferred form, a bolt is used to transfer membrane "tension" loads to axial thrust bearing 121. It should be understood that bearing 121 could take other forms providing rolling, sliding, or other bearing support.

Although not rotating, it should be appreciated that membranes 21 and 31 are continuously being flexed during operation of pump 10 placing stress on the material forming membrane 21. To improve membrane life, membranes 31 and/or 21 could include directional stiffness/flexibility characteristics and specifically should be flexible in at least one direction in order to deform into the nonconcentric shape with a minimum of stress while substantially preventing deflection of the membrane by being nonflexible in other directions to maintain stiffness in the direction to withstand the loads and dynamic forces imposed by the high-speed rotation of fluids necessary to generate pumping force or pressure. For example, directional surface corrugations or surfaces, not shown, could be integrally formed in hose 14 inside of the pumping chamber. It should further be appreciated that in the preferred form, such surface corrugations could provide flow control surfaces to direct rotary motion to the fluid and improve energy transfer between membranes 31 and/or 21 and the rotating fluid and to improve pump efficiency. However, the directional stiffness/flexibility characteristics can be provided by other techniques including but not limited to fabric reinforcement or rigid stiffeners in membranes 31 and/or 21 themselves.

An alternate or additional fluid inlet 81 to inlet 71 may be provided to the pumping chamber through deformer 41. Particularly, in the preferred form as shown in FIG. 2, shaft 44 and shaft extension 45 are hollow. Membranes 31 and/or 21 can include a tube liner 51 integrally formed or interconnected with tube 14 and extending concentrically inside the hollow shaft 44 and shaft extension 45 and tube 14, with liner 51 forming and defining inlet 81. It can then be appreciated that as fluid enters the pumping chamber through inlet 81, the fluid travels at a relatively constant axial speed, but with a gradually increasing rotational velocity. Therefore, the fluid is not subject to sudden accelerations. This feature is especially important in the pumping of easily damageable fluids such as food, drugs, chemicals, and body fluids including blood. Further, this feature allows pump 10 to pump a high percentage of vapor bubbles without becoming vaporlocked. Specifically, pump 10 can be designed with internal fluid speeds high enough to carry the bubbles through the pump inlet using fluid dynamic drag forces. Once the bubbles are in the pump chamber, the vapor and fluid will separate due to centrifugal forces, and the vapor can be removed separately if desired. (This could allow pump 10 to be used as an air/vapor compressor or vacuum pump for toxic materials in place of a "liquid ring" style of vapor pump). In conventional centrifugal pumps, low internal radial fluid velocities result in low fluid dynamic drag forces which cannot overcome the buoyant forces, resulting in a vapor core filling the pump preventing the device from pumping.

Figure 3:
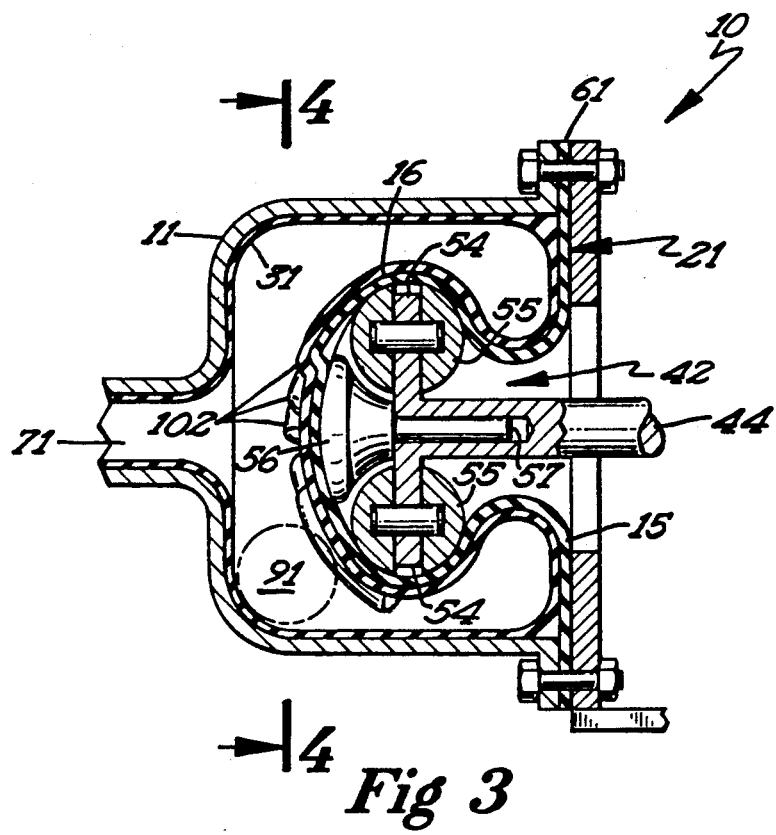
FIG. 3 shows a cross sectional view of an alternate embodiment of a flexible membrane sealless centrifugal pump according to the preferred teachings of the present invention.
Figure 4:
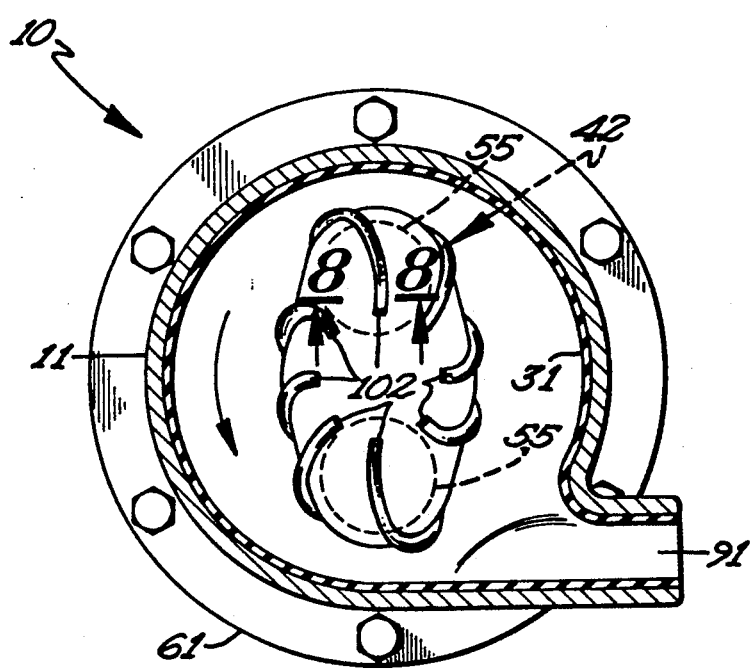
FIG. 4 shows a cross sectional view of the flexible membrane sealless pump of FIG. 3.

Although the single lobe design created by shaft extension 45 of pumps 10 of FIGS. 1 and 2 is rotationally unbalanced, conventional balancing weights can be supplied inside electric motor 131 to provide dynamic balance for deformer 41 and pump 10. However, a balanced double lobe deformer 42 such as the type shown in FIGS. 3, 4, and 8 can be utilized to overcome balancing problems. Particularly, in the preferred form, membrane 21 includes a tube 16 shown in the preferred form as being teardrop-shaped and having an open end and generally annular, circular cross sections, with tube 16 extending inwardly into the interior of pump housing 11. Deformer 42 is located outside of the pumping chamber and inside tube 16 and includes first and second radial flanges 54 extending generally perpendicularly and on dynamically opposite sides of driving shaft 44. First and second, semispherical rollers 55 are rotatably mounted on opposite sides of each flange 54 about an axis parallel to and spaced from the center of fluid rotation and shaft 44.

It can then be appreciated that deformer 42 is generally T-shaped and deflects membranes 31 and/or 21 into a symmetrical but nonconcentric shape and particularly a shape having generally oval cross sections along planes perpendicular to drive shaft 44 and the center of fluid rotation. It can then be appreciated that with rotation of drive shaft 44 by motor 131, deformer 42 rotates the noncircular, oval shape about an axis defined by shaft 44 to function as a rotating pump impeller causing the fluid inside the pumping chamber to rotate and be discharged through outlet 91 in the same manner as a conventional pump design.

Deformer 42 can include provisions for reducing friction and wear due to axial loads shown in the preferred form as a head portion 56 abutting with membrane 21 generally axially from driving shaft 44. Head portion 56 does not rotate relative to membrane 21 but is rotatably mounted to shaft 44 by a stem 57 extending axially from portion 56 and slideably received in an axial bore formed in shaft 44. Similarly, although rollers 55 reduce friction and wear due to radial loads, deformer 42 can include further provisions for reducing friction and wear due to radial loads such as bearings for the axles of rollers 55, a sock-like member inside of membrane 21, and/or a planetary gearing mechanism for causing rotation of rollers 55 about their axles when deformer 42 is rotated by motor 131. As with deformer 41, membrane 21 can include provisions for improving energy transfer and/or for extending life of membrane 21 such as surface corrugations 102 as shown. In the preferred form, corrugations 102 are at nonperpendicular angles to the fluid rotation and in the preferred form are generally helix-shaped.

Whereas deformers 41 and 42 are positioned interiorly of membrane 21, it is desirable in certain applications to deform membrane 21 from the exterior of membrane 21 and outside of the pumping chamber. Pump 10 of a balanced design according to the preferred teachings of the present invention is shown in FIGS. 5, 6, and 7 including a deformer 43 for deflecting membrane 21 from the outside. Particularly, membrane 21 includes a tube 17 shown in the preferred form as being funnel-shaped or cone-shaped having annular, circular cross sections, with tube 17 extending outwardly from the interior of pump housing 11. In the preferred form, tube 17 has an open end forming and defining the primary fluid inlet, with inlet 71 being alternately or additionally provided. Deformer 43 includes a hollow spindle 64 located outside of tube 17 and concentrically thereto and the center of fluid rotation. Spindle 64 is rotated about an axis extending in the preferred form along the center of fluid rotation by any suitable means such as an electric motor 133. First and second rollers 65 are rotatably mounted by shafts 66 to spindle 64 about axes which in the preferred form are parallel to and dynamically spaced on opposite sides of the center of fluid rotation. Rollers 65 deflect membranes 31 and/or 21 into a symmetrical but nonconcentric shape and particularly a shape having generally oval cross sections along planes perpendicular to the rotational axis of spindle 64 and the center of fluid rotation. It can then be appreciated that with rotation of spindle 64 by motor 133, deformer 43 rotates the nonconcentric, oval shape about an axis defined by the rotational axis of spindle 64 to function as a rotating pump impeller causing fluid inside membrane 21 defining the pumping chamber to rotate and be discharged through outlet 91 in the same manner as a conventional centrifugal pump design.

Although rollers 65 reduce friction and wear due to radial loads, deformer 43 can include further provisions for reducing friction and wear. For example, deformer 43 can include bearings for shafts 66 of rollers 65, a sleeve-like member outside of membrane 21, and/or a planetary gearing mechanism for causing rotation of rollers 65 about shafts 66 when deformer 43 is rotated by motor 133. As with deformers 41 and 42, membrane 21 can include provisions for improving energy transfer and/or for extending life of membrane 21 such as surface corrugations 103 located inside the pumping chamber as shown. In the preferred form, corrugations 103 are of the same type as corrugations 102 shown in FIG. 8 and are at nonperpendicular angles to the fluid rotation and in the preferred form are generally helix-shaped.

It should then be appreciated that pump 10 according to the preferred teachings of the present invention uses nonrotatable, flexible, impervious membrane 21 to completely separate the pumped fluid from moving, sliding, and/or rubbing pumping machinery. Further, the rotation of the fluid to be pumped is caused by deforming or deflecting membrane 21 into a nonconcentric shape, with the shape being rotated by the pump machinery but without requiring membrane 21 to rotate. Particularly, membrane 21 is deformed without rotation by deformers 41, 42, and 43 in the preferred forms of pumps 10 of the present invention which have rotary motion and which are separated from the fluid by membrane 21. Thus, pump 10 does not use a conventional rotating shaft seal to seal rotating drive shaft 44 as in conventional centrifugal pumps (and thus also eliminates the requirement of injecting a sealing fluid into a rotating shaft seal area to flush away troublesome material as utilized in conventional centrifugal pumps), does not use internal bearings within the pumped fluid as in conventional magnetic drive pumps, does not use internal intake/discharge valves as in conventional positive displacement pumps, nor any other moving, sliding, and/or rubbing surfaces within the pumped fluid and which can cause damage to fragile fluids being pumped. It can then be appreciated that pump 10 according to the teachings of the present invention is constructed of components of a simple design which can be manufactured with relatively loose tolerances and at very low costs in comparison to components for conventional pumps.

Membrane 31 which could be formed of one or more layers according to the teachings of the present invention and is believed to be particularly advantageous. Specifically, as membrane 31 only needs to flex and not rotate in order to pump the fluid, membrane 31 could be a low cost "throw-away" component like a two-fingered surgical glove to line the inside of the pump chamber with a low cost replaceable liner to prevent the pumped fluid from contacting the other pump components and to simplify the cleaning and sterilization of pump 10. Further, the area between membranes 21 and 31 could be sealed and contain a predetermined test pressure so that if membrane 31 failed, an instrument monitoring the test pressure would detect the change in test pressure and shut down pump 10 while membrane 21 and/or additional layers of membrane 31 prevented leaks.

Membranes 21 and 31 can be made from any flexible material including but not limited to elastomers, metal, or any other material which possesses the required elasticity or flexibility. For example, since membranes 21 and 31 only need to flex and not rotate in order to pump, the use of live donor tissue would be possible as structural material forming membrane 21 or 31. The live tissue would be biocompatible with blood and other human fluids, when the fluids need to be pumped through artificial organs to maintain life after the body's natural organs have failed, with the live donor tissue having the potential to regenerate itself and not wear out. Similarly, pump 10 could use a length of flexible high pressure hydraulic hose for membrane 21, which means pump 10 according to the teachings of the present invention could have a pressure rating of 1000 psi (70 kilograms per square centimeter) or more. To achieve very high discharge pressures, it will be necessary to use a multistage pump design, since centrifugal pumps have a typical pressure increase of about 100 psi (7 kilograms per square centimeter) maximum for each pump stage.

Pump 10 according to the teachings of the present invention is potentially suitable for pumping blood including use as an artificial heart because there is no rotating shaft seal to leak, there are no internal bearings or other close moving clearances to damage the blood, there is a very gentle pumping action because there are no sudden transitions from a slow moving fluid inlet into a high speed impeller to cause turbulence and damage to the blood, and there is no need for stagnant areas to cause blood clots. Likewise, pumps 10 according to the teachings of the present invention is particularly applicable for pumping foods and biological fluids due to the ease of cleaning, for pumping toxic chemical fluids and in aerospace applications due to the leakproof design, for pumping abrasive slurries due to the absence of rotating shaft seals or bearings in the pumped fluids, and for pumping material which is stringy and/or tends to clog close moving surfaces such as those in intake or discharge valves. Further, pumps 10 according to the teachings of the present invention can be run "dry" or run without fluid without damage as can occur in magnetic drive pumps. Furthermore, pumps 10 can inherently pump a large amount of vapor without becoming vaporlocked. Similarly, pumps 10 according to the teachings of the present invention will be suitable for suction lift and high vacuum pumping, especially since air can not leak into pumps 10 according to the teachings of the present invention through a leaky rotating shaft seal. Likewise, pumps 10 according to the teachings of the present invention are suitable for pumping fluids containing both vapor bubbles and solids, either as a two-phase fluid or as a three-phase fluid.

As set forth previously with respect to pump 10 of FIG. 2, pumps 10 according to the teachings of the present invention can be designed with internal fluid velocities high enough to carry vapor bubbles through the pump inlet into the pumping chamber using fluid dynamic drag forces Thus, pump 10 according to the teachings of the present invention is able to pump fluid having a high percentage of vapor bubbles.

Pump 10 according to the teachings of the present invention has very favorable "net positive suction head" characteristics, and, as a result, cavitation problems are minuscule. The Bernoulli equation indicates that an increase in fluid velocity will result in a decrease in fluid pressure. If the pressure decreases below the vapor pressure of the fluid, cavitation vapor bubbles will form. When the vapor bubbles flow downstream to a higher pressure region, the cavitation bubbles can collapse with enough force to damage anything in the area. In conventional centrifugal pumps, the inlet fluid must suddenly contact the high velocity impeller surface, which may cause cavitation. However, pumps 10 according to the teachings of the present invention do not require a sudden transition from a low velocity fluid inlet to a high velocity impeller surface, so the possibility of cavitation is minuscule.

Now that the basic teachings of the present invention have been explained, many extensions and variations will be obvious to one having ordinary skill in the art. For example, although in the preferred form primary membrane 21 closes off an end of pump housing 11, housing 11 could include a rigid end having a nipple upon which primary membrane 21 in the form of a hose is statically secured such as by a hose clamp. Similarly, membrane 21 can have other shapes having the ability to be deformed to rotate fluid in the pumping chamber to generate a kinetic/centrifugal force sufficient to produce a pumping action and which separates the machinery used to deform membrane 21 from the fluid according to the teachings of the present invention.

Likewise, although deformers 41, 42, and 43 have been shown and described and are believed to be particularly advantageous, pumps 10 can include other types and forms of machinery for deforming flexible membrane 21 into a nonconcentric shape to rotate the fluid to be pumped in the pumping chamber without requiring membrane 21 to rotate and in the preferred form to rotate the nonconcentric shape about an axis extending along the center of fluid rotation according to the teachings of the present invention.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Pump for pumping fluid comprising, in combination: a pumping chamber to contain the fluid; a flexible membrane forming at least a portion of the pumping chamber; means located outside of the pumping chamber for deforming the flexible membrane to rotate the fluid in the pumping chamber about a center of fluid rotation to generate a centrifugal force to produce a pumping action; a fluid outlet extending into the pumping chamber spaced from the center of fluid rotation and providing a continuously open passage for the fluid when the flexible membrane is being deformed; and a fluid inlet extending into the pumping chamber radially inwardly from the fluid outlet and providing a continuously open passage for the fluid when the flexible membrane is being deformed.

2. The pump of claim 1 wherein the deforming means comprises means for deforming the flexible membrane into a nonconcentric shape relative to the center of fluid rotation.

3. The pump of claim 2 wherein the deforming means comprises means for rotating the nonconcentric shape in a rotary manner about the center of fluid rotation.

4. The pump of claim 3 wherein the fluid outlet extends generally tangentially from the fluid rotation.

5. The pump of claim 1 wherein the flexible membrane includes a tube extending into the pumping chamber, with the tube having an open end, an interior, and generally circular cross sections; and wherein the deforming means comprises, in combination: a driving shaft extending through the open end and into the interior of the tube along the center of fluid rotation; means rotatable with the driving shaft for deflecting the tube into a nonconcentric shape relative to the center of fluid rotation; and means for rotating the driving shaft.

6. The pump of claim 5 wherein the deflecting means has an end opposite to the driving shaft; and wherein the pump further comprises, in combination: means for reducing friction from axial thrust loads between the end of the deflecting means and the flexible membrane.

7. The pump of claim 6 further comprising, in combination: means for reducing friction from radial loads between the deflecting means and the flexible membrane.

8. The pump of claim 5 further comprising, in combination: means for reducing friction from radial loads between the deflecting means and the flexible membrane.

9. The pump of claim 5 further comprising, in combination: a secondary membrane positioned on the flexible membrane opposite to the deflecting means.

10. The pump of claim 5 wherein the deflecting means deflects the tube in a nonsymmetrical shape from the center of fluid rotation.

11. The pump of claim 10 wherein the deflecting means comprises a shaft extension integrally extending at an angle from the driving shaft.

12. The pump of claim 11 wherein the driving shaft and the shaft extension are hollow; wherein the membrane includes an integral tube liner extending concentrically inside of the hollow driving shaft and the shaft extension; and wherein the fluid inlet is formed by and defined by the tube liner.

13. The pump of claim 12 further comprising, in combination: a secondary, stationary, fluid inlet extending into the pumping chamber radially inwardly from the fluid outlet.

14. The pump of claim 11 wherein the shaft extension includes an end opposite to the driving shaft; and wherein the pump further comprises, in combination: means for reducing friction from axial thrust loads between the end of the shaft extension and the flexible membrane.

15. The pump of claim 14 further comprising, in combination: means for reducing friction from radial loads between the shaft extension and the flexible membrane.

16. The pump of claim 11 further comprising, in combination: means for reducing friction from radial loads between the shaft extension and the flexible membrane.

17. The pump of claim 11 further comprising, in combination: a secondary membrane positioned on the flexible membrane opposite to the shaft extension.

18. The pump of claim 5 further comprising, in combination: flow control surfaces on the flexible membrane opposite the deflecting means for directing rotary motion to the fluid.

19. The pump of claim 5 wherein the deflecting means deflects the tube in a symmetrical shape from the center of fluid rotation.

20. The pump of claim 19 wherein the deflecting means is generally T-shaped and includes first and second portions extending generally perpendicular from the center of fluid rotation.

21. The pump of claim 20 wherein the first and second portions have opposite ends engaging the interior of the tube; and wherein the pump further comprises, in combination: means for reducing friction and wear due to radial loads.

22. The pump of claim 21 wherein the radial load reducing means comprises, in combination: rollers for engaging the flexible membrane carried by the first and second portions.

23. The pump of claim 22 further comprising, in combination: means for reducing friction and wear due to axial loads.

24. The pump of claim 23 wherein the axial load reducing means comprises, in combination: a head portion for abutting with the flexible membrane generally axially from the driving shaft; and means for rotatably mounting the head portion to the driving shaft.

25. The pump of claim 19 further comprising, in combination: flow control surfaces on the flexible membrane opposite the deflecting means for directing rotary motion to the fluid.

26. The pump of claim 1 wherein the flexible membrane includes a tube having an interior, and generally annular cross sections; with the fluid rotating in the interior of the flexible membrane; and wherein the deforming means comprises, in combination: means located outside of the flexible membrane for deflecting the tube into a nonconcentric shape relative to the center of fluid rotation; and means for rotating the deflecting means about the center of fluid rotation.

27. The pump of claim 26 wherein the deflecting means comprises, in combination: at least a first roller spaced from the center of fluid rotation and engaging the flexible membrane for rotation about an axis.

28. The pump of claim 27 wherein the rotating means comprises, in combination: a hollow spindle arranged generally concentrically to the flexible membrane and rotatable about the center of fluid rotation, with the first roller being rotatably mounted to the spindle; and means for rotating the spindle.

29. The pump of claim 26 further comprising, in combination: flow control surfaces in the interior of the flexible membrane opposite the deflecting means for directing rotary motion to the fluid.

30. The pump of claim 26 further comprising, in combination: a secondary membrane positioned on the flexible membrane inside of the internal pocket and opposite to the deflecting means.

31. The pump of claim 26 wherein the tube has an open end, with the open end of the tube forming and defining the fluid inlet.

32. The pump of claim 31 further comprising, in combination: a secondary, stationary, fluid inlet extending into the pumping chamber radially inwardly from the fluid outlet.

33. Device for rotating a fluid in a pumping chamber about a center of fluid rotation and with a tangential velocity to generate a centrifugal force to produce a pumping action comprising, in combination: a nonrotatable membrane deformable in a nonconcentric shape from the center of fluid rotation and flexible to rotate the nonconcentric shape in a rotary manner about the center of fluid rotation; and means on the nonrotatable membrane for substantially preventing deflection of the membrane in at least first directions while allowing flexing in other directions in order to deform into the nonconcentric shape.

34. The device of claim 33 wherein the flexing preventing and allowing means comprises, in combination: corrugations formed in the nonrotatable membrane.

35. The device of claim 34 wherein the corrugations are at nonperpendicular angles to the fluid rotation.

36. The device of claim 33 wherein the membrane is in the form of a tube having an interior, with the fluid located in the interior of the tube.

37. The device of claim 33 wherein the membrane is in the form of a tube having an interior, with the fluid located outside of the tube.

38. Device for rotating a fluid in a pumping chamber about a center of fluid rotation comprising, in combination: a nonrotatable membrane deformable in a nonconcentric shape from the center of fluid rotation and flexible to rotate the nonconcentric shape in a rotary manner about the center of fluid rotation, with the nonconcentric shape having a size and configuration to transfer energy to the fluid and maximize the tangential velocity of the fluid rotation to generate a centrifugal force to produce a pumping action.

39. The device of claim 38 further comprising, in combination: means on the nonrotatable membrane for substantially preventing deflection of the membrane in at least first directions while allowing flexing in other directions in order to deform into the nonconcentric shape.

40. The device of claim 38 wherein the membrane is in the form of a tube having an interior, with the fluid located in the interior of the tube.

41. The device of claim 40 wherein the tube is hose-shaped having generally equal cross sections.

42. The device of claim 40 wherein the tube is teardrop-shaped.

43. The device of claim 40 further comprising, in combination: a tube liner located in the interior of the tube allowing fluid flow to the pumping chamber, with the tube liner being interconnected to the tube in a nonrotatable manner.

44. The device of claim 43 wherein the tube liner is deformable and flexible with the tube.

45. The device of claim 38 wherein the membrane is in the form of a tube having an interior, with the fluid located outside of the tube.

46. The device of claim 45 wherein the tube is cone-shaped.

47. Device for rotating a fluid in a pumping chamber about a center of fluid rotation to generate a centrifugal force to produce a pumping action comprising, in combination: a nonrotatable membrane deformable in a nonconcentric shape from the center of fluid rotation and flexible to rotate the nonconcentric shape in a rotary manner about the center of fluid rotation; and means on the nonrotatable membrane for directing fluid flow to transfer the rotary motion of the nonconcentric shape to the fluid in the pumping chamber.

48. The device of claim 47 wherein the directing means comprises, in combination: corrugations formed in the nonrotatable membrane.

49. The device of claim 48 wherein the corrugations are at nonperpendicular angles to the fluid rotation.

50. The device of claim 47 wherein the membrane is in the form of a tube having an interior, with the fluid located in the interior of the tube.

51. The device of claim 47 wherein the membrane is in the form of a tube having an interior, with the fluid located outside of the tube.

* * * * *